(12) United States Patent
Neuba et al.

(10) Patent No.: US 8,845,759 B2
(45) Date of Patent: Sep. 30, 2014

(54) REDUCTION OF AMMONIA SMELL IN SUBSTANCES FOR OXIDATIVE DYEING AND/OR LIGHTENING KERATIN FIBRES

(71) Applicant: Henkel AG & Co. KGaA, Dusseldorf (DE)

(72) Inventors: Constanze Neuba, Dusseldorf (DE); Frank Janssen, Dusseldorf (DE)

(73) Assignee: Henkel AG & Co. KGAA, Dusseldorf (DE)

( * ) Notice: Subject to any disclaimer, the term of this patent is extended or adjusted under 35 U.S.C. 154(b) by 0 days.

(21) Appl. No.: 14/103,572

(22) Filed: Dec. 11, 2013

(65) Prior Publication Data

US 2014/0165299 A1    Jun. 19, 2014

(30) Foreign Application Priority Data

Dec. 14, 2012    (DE) .......................... 10 2012 223 204

(51) Int. Cl.
*A61Q 5/10*    (2006.01)
*A61K 8/49*    (2006.01)

(52) U.S. Cl.
CPC .. *A61K 8/498* (2013.01); *A61Q 5/10* (2013.01)
USPC ................................................. 8/405; 8/406

(58) Field of Classification Search
CPC ........... A61Q 5/10; A61K 8/22; A61K 8/342; A61K 8/498
USPC ..................................................... 8/405, 406
See application file for complete search history.

(56) References Cited

U.S. PATENT DOCUMENTS

2010/0183527 A1 * 7/2010 Moser et al. .................... 424/59

FOREIGN PATENT DOCUMENTS

| JP | 2007191459 A | 8/2007 |
|---|---|---|
| JP | 2003040750 A | 2/2013 |
| WO | 2005110499 A1 | 11/2005 |
| WO | 2006060565 A2 | 6/2006 |
| WO | 2006060570 A2 | 6/2006 |

OTHER PUBLICATIONS

STIC Search Report dated Feb. 5, 2014.*

* cited by examiner

*Primary Examiner* — Eisa Elhilo
(74) *Attorney, Agent, or Firm* — Ingrassia Fisher & Lorenz, P.C.

(57) ABSTRACT

A preparation for oxidative dyeing and/or lightening keratin fibers, particularly human hair, contains in a cosmetic carrier (a) a first alkyl glucoside having formula (I)

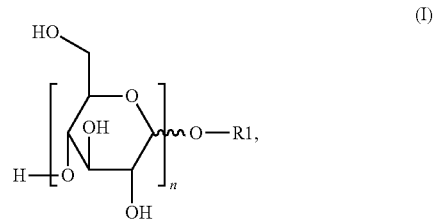

(I)

in which R1 stands for an unbranched or branched, saturated or unsaturated $C_{20}$-$C_{28}$ alkyl group and n stands for a whole number from 1 to 10, (b) a second alkyl glucoside having formula (II)

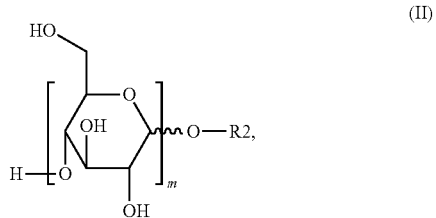

(II)

in which R2 stands for an unbranched or branched, saturated or unsaturated $C_8$-$C_{18}$ alkyl group and m stands for a whole number from 1 to 10, (c) ammonia and (d) an oxidizer.

15 Claims, No Drawings

REDUCTION OF AMMONIA SMELL IN SUBSTANCES FOR OXIDATIVE DYEING AND/OR LIGHTENING KERATIN FIBRES

CROSS-REFERENCE TO RELATED APPLICATION

This application claims priority to German Patent Application No. 10 2012 223 204.4, filed Dec. 14, 2012 the entire contents of which is encorporated herein by reference.

TECHNICAL FIELD

The technical field relates to preparations for oxidative dyeing and/or lightening of keratin fibres, particularly human hair, containing a combination of two alkyl glucosides having alkyl chains of various lengths, ammonia, and at least one oxidising agent in a cosmetic carrier. The technical field further relates to the use of the combination to reduce the ammonia smell before, during and after the dyeing and/or lightening process.

BACKGROUND

In order to prepare colour-altering cosmetic substances, particularly for keratin fibres such as hair, a person skilled in the art is familiar with various dyeing systems depending on the requirements the colouring must satisfy. For permanent, intense dyeing with corresponding fastness properties, substances called oxidation dyes are used. Such dyes typically contain oxidation dye precursors, also called "developer and coupler components", which combine with each other to form the actual dyes under the effects of oxidising agents such as hydrogen peroxide. Oxidation dyes are notable for their excellent, long-lasting colouring results. Besides dyeing, many consumers are particularly fond of lightening their hair or giving it a more blond appearance. For this, the natural or synthetic dyes that colour the hair fibres are mostly bleached oxidatively by the action of corresponding oxidising agents, such as hydrogen peroxide.

In order to develop a satisfactory dyeing and lightening effect, oxidative dyeing and lightening agents generally need an alkaline pH value during application. Optimal results are obtained particularly with pH values between 8.5 and 10.5.

Until the present time, the alkalising agent of choice for adjusting these pH values has been ammonia. With ammonia, not only is it possible to set the pH range required for forming the dye, but ammonia lends body to the hair more effectively than any other known alkalising agent. At the same time, ammonia functions as a penetrating agent and a penetrating auxiliary agent—also more effectively than all other commercially available alkalising agents.

This is why, when ammonia is used in oxidative dyes, significantly better results are obtained in terms of colour intensity and grey coverage than with other alkalising agents (such as potassium or sodium hydroxide, alkanolamines, or carbonates such as sodium carbonate or potassium carbonate).

As the colours are more intense from the outset, so the fastness properties of the hair dyes produced with the aid of ammonia are also improved. In particular, coloured hair exhibits the best washing fastness properties when ammonia has been chosen as the alkalising agent.

The use of ammonia brings so many different technical application advantages that ammonia is used in a large number of commercially available oxidative dyeing and lightening products even despite its unpleasant, acrid smell.

Extensive efforts to temper the smell of ammonia are already known from the literature. In this context, approaches for minimising the odour fall into three basic groups: according to the literature, the first option is to change the alkalising substance, and thus partially or completely replace ammonia with odourless agents.

Accordingly, many formulations exist that, for example, use a mixture of ammonia and monoethanolamine or monoethanolamine alone as the alkalising agent. However, the result of completely or partially replacing ammonia is that the dyes generally do not penetrate the hair as well, which in turn leads in particular to less satisfactory grey coverage and poorer washing fastness, as described in the preceding. If the development of particularly long-lasting shade variations is important, the use of monoethanolamine is therefore not a viable option.

Documents WO 2006060570 and WO 2006060565 suggest the use of carbonates or carbonate sources as alkalising agents for preparing oxidative dyes with low odour. However, it is also known from the literature that when used together with oxidising agents, carbonates can severely damage hair. The additional hair damage caused by the carbonates may not be a major cause for concern when the dye is used on untreated or undamaged hair, but for individuals who regularly colour or lighten their hair, severe cumulative damage may be caused. If more pronounced lightening and/or regular dyeing is desired, the use of carbonates also does not represent an acceptable alternative.

A second general approach for reducing the smell of ammonia consists in the addition of special perfumes that are intended to hide the smell. This route is adopted in WO 2005/110499 for example. However, perfumes can be unstable under the alkaline storage conditions, and there is a risk that the fragrances may be decomposed or the structure thereof may be altered during storage, resulting in an unpredictable alteration of the smell. Since such alterations often do not become noticeable until several months or even years later, the use of new and/or unknown perfumes is to be regarded as unreliable.

A third general approach for diminishing the smell of ammonia consists in an optimisation of the formulation. In this case, the objective is to select the carrier components of the formulation in such manner that they ensure as much of the ammonia as possible is retained inside the formulation, thereby minimising its odour. However, it is also known that the formulation, the lipids, emulsifiers, tensides it contains, and the viscosity thereof have a significant effect on colouring performance. If the formulation is modified, it is therefore essential to ensure that the colouring performance is not impaired thereby.

As examples of such, JP 2007191459 suggests the use of cationic tensides, phosphate esters and aliphatic alcohols in order to reduce the smell of ammonia in hair dyeing agents. JP 2003040750 discloses that the ammonia odour in lightening agents is particularly weak when at least 5% of a crystalline component is added to them.

It is particularly difficult to devise a solution that will minimise the odour for the entire period for which the application lasts. The period for which the user of hair colouring products is in contact with the dyeing agent lasts from the production of the application mixture, throughout the time when it is applied to the hair, and the time required for it to take effect until the formulation is washed out. Given typical working times from about 30 to about 45 minutes, the entire process can take up to 90 minutes, in extreme cases even as long as two hours. Providing a solution for covering the smell of ammonia that remains effective for this entire period poses an extremely difficult challenge. Precisely in this field, there is significant need for improvement, and as yet there is no optimal solution known from the prior art for reducing the smell of ammonia.

The problem addressed by the present invention was therefore to provide oxidative agents for dyeing and/or lightening the colour of hair that have a less pronounced smell of ammonia. At the same time, the use of such agents should not lead to any loss of colouring performance, particularly grey coverage, or washing fastness. Moreover, the use of such agents should not be associated with greater hair damage.

DETAILED DESCRIPTION

In this context, it was a particular task of the present invention to achieve a reduction in the smell of ammonia that would last for the entire application period. Even by the end of the application, the perception of the ammonia smell should still be effectively minimised.

Surprisingly, it was found in the course of the work leading to the present invention that it is possible to effectively minimise the perception of the smell of ammonia in agents for dyeing and/or lightening keratin fibres for the entire application period, if in addition to an oxidiser and ammonia a combination of two different alkyl glucosides with alkyl chains of different lengths is also added to the agents.

A first object of the present invention is therefore an agent for oxidative colouring and/or lightening keratin fibres, particularly human hair, containing in a cosmetic carrier
(a) at least one first alkyl glucoside having formula (I)

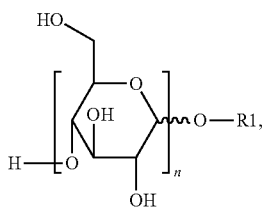

in which R1 stands for an unbranched or branched, saturated or unsaturated $C_{20}$-$C_{28}$ alkyl group, and
n stands for a whole number from 1 to 10,
(b) at least one second alkyl glucoside having formula (II)

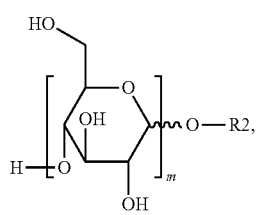

in which R2 stands for an unbranched or branched, saturated or unsaturated $C_8$-$C_{18}$ alkyl group, and
m stands for a whole number from 1 to 10,
(c) ammonia and
(d) at least one oxidising agent.

The term keratin-containing fibres is generally understood to refer to all animal hair, including for example wool, horsehair, angora hair, furs, feathers and products or textiles manufactured therefrom. In this instance, however, when keratin fibres are discussed the reference is mainly to human hair.

The term "agents for dyeing and/or lightening" keratin fibres used according to the invention denotes oxidative dyes and oxidative lightening agents (agents for lightening hair colour). Oxidative dyes contain oxidation dye precursors, also called developer and coupler components. Developers and couplers diffuse separately into the keratin fibres and react with each other under the effects of ammonia as the alkalising agent and an oxidiser (usually hydrogen peroxide) to form the actual dyes. At the same time, the keratin fibre becomes lighter to a greater or lesser degree during the dyeing process depending on the quantity of oxidiser used, because the oxidiser not only initiates the dye formation process from the developers and couplers, it also destroys the hair's intrinsic pigments (melanin) by oxidation.

Thus, depending on the quantity of oxidation dye precursors and of the oxidiser, oxidative dyeing may primarily serve to colour the hair (with a high proportion of dye) or primarily to lighten the hair (with a high proportion of oxidiser). In the latter case, the oxidation dye precursors are used mainly to provide colour variations in the final lightening effect.

Oxidative bleaching agents may also contain oxidation dye precursors in order to create highlights, but if simple lightening without additional colour variations is desired, they may also be free from oxidation dye precursors. For moderate lightening, hydrogen peroxide (typically in the form of an aqueous solution thereof) is often used alone as the oxidiser in oxidative bleaching agents. If a more pronounced lightening effect is desired, hydrogen peroxide may also be used in combination with other stronger oxidisers such as persulphate salts (ammonium peroxodisulphate, sodium peroxodisulphate and/or potassium peroxodisulphate).

The agents according to the invention contain the essential components for the invention in a cosmetic carrier, preferably in a suitable aqueous, alcohol or aqueous-alcohol carrier. For the purpose of colouring hair, such carriers are for example creams, emulsions, gels, or also tenside-containing foaming solutions, such as shampoos, aerosol foams, foam formulations or other preparations that lend themselves to use on the hair.

As a first essential component of the formulation, the agents according to the invention contain at least one alkyl glucoside (a) having formula (I)

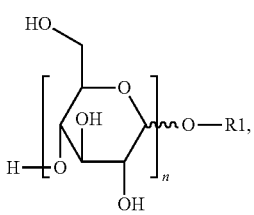

in which R1 stands for an unbranched or branched, saturated or unsaturated $C_{20}$-$C_{28}$-alkyl group, and n stands for a whole number from 1 to 10.

The term unbranched alkyl group is understood to mean a linear alkyl group. For the purposes of the present invention, alkyl glucosides are understood to be the glycosides of glucose, wherein glycosidic bonding takes place in the form of a condensation reaction with the alcohol OH group of a $C_{20}$-$C_{28}$ hydroxyalkyl radical starting from the anomeric hydroxyl group of the glucose radical (in the present case in the pyranose form thereof).

The glycosidic functionality is created starting from glucose in the pyranose form thereof, and both the glucosides starting from α-glucose (formula Ia) and from β-glucose (formula Ib) are included in the scope of the invention.

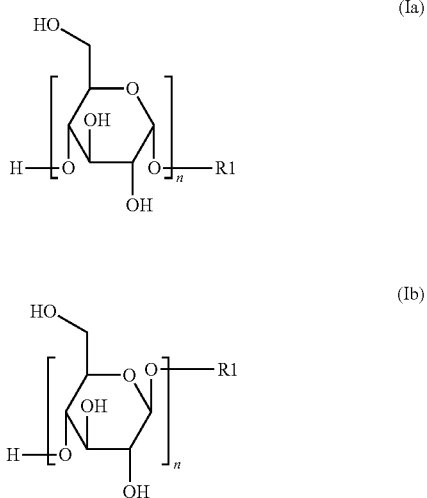

Radical R1 stands for an unbranched or branched, saturated or unsaturated $C_{20}$-$C_{28}$ alkyl group, and n stands for a whole number from 1 to 10.

It was found that the ammonia odour is minimised particularly effectively when the radical R1 stands for an unbranched, saturated $C_{20}$-$C_{24}$ alkyl group, preferably an unbranched, saturated $C_{20}$-$C_{22}$ alkyl group, and particularly preferably an unbranched, saturated $C_{20}$ alkyl group.

The problem as defined according to the invention is solved particularly effectively when n stands for a number from 1 to 4, preferably for the numbers 1 and 2, and particularly preferably the number 1.

In a most particularly preferred form, the compound (Ic) is used as the alkyl glucoside having formula (I).

In a particularly preferred embodiment, am agents for dyeing and/or lightening keratin fibres is therefore characterized in that it contains at least one compound having formula (I) as the first alkyl glucoside (a), in which R1 stands for an unbranched, saturated $C_{20}$ alkyl group and n stands for the number 1.

A corresponding, particularly preferred alkyl glucoside (a) with R1 equal to a $C_{20}$ alkyl group is known by the trade name Montanov 202, for example.

In particular, the ammonia smell is also minimised effectively when the one or more alkyl glucosides (a) with formula (I) are used within certain quantity ranges. The one or more alkyl glucosides (a) having formula (I) are used particularly preferably in a total quantity from about 0.3 to about 4.5% by weight, preferably from about 0.5 to about 3.5% by weight, more preferably from about 0.7 to about 2.5% by weight, and most preferably from about 0.9 to about 1.5% by weight—relative to the total weight of the ready-to-use preparation in each case.

In a further particularly preferred embodiment, a preparation according to the invention is therefore characterized in that it contains one or more alkyl glucosides (a) having formula (I) in a total quantity from about 0.3 to about 4.5% by weight, preferably from about 0.5 to about 3.5% by weight, more preferably from about 0.7 to about 2.5% by weight, and most preferably from about 0.9 to about 1.5% by weight—relative to the total weight of the ready-to-use preparation in each case.

As the second essential formulation component, the agents contain at last one more alkyl glucoside (b) having formula (II)

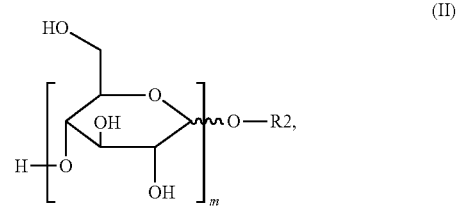

in which R2 stands for an unbranched or branched, saturated or unsaturated $C_8$-$C_{18}$ alkyl group, and m stands for a whole number from 1 to 10.

The formation of glucosides having formula (II) also takes place starting from glucose in the pyranose form thereof, and here too the glucosides starting from α-glucose (formula IIa) and from β-glucose (formula IIb) are included in the scope of the invention.

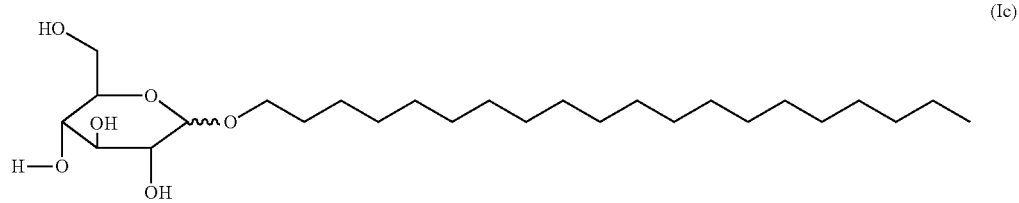

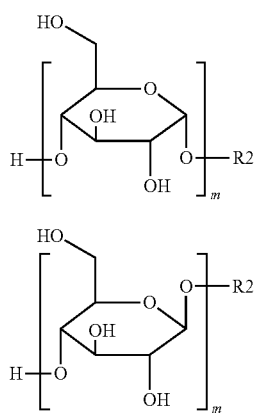

(IIa)

(IIb)

If selected representatives of alkyl glucosides having formula (II) are used in conjunction with the additional essential components (a), (c) and (d) in the preparation according to the invention, the odour of ammonia can be suppressed particularly well, effectively, and for a long period.

It is therefore preferable if the radical R2 stands for an unbranched, saturated $C_{12}$-$C_{18}$ alkyl group. Radical R2 stands more preferably for a linear saturated $C_{14}$-$C_{16}$-alkyl group, and radical R2 most particularly preferably stands for a linear saturated $C_{16}$-$C_{18}$ alkyl group.

With regard to the perception of the smell of ammonia, it is further advantageous if m stands for a whole number from 1 to 4. Yet more preferably, m stands for the numbers 1 or 2, and explicitly most particularly preferably m stands for the number 1.

Most particularly preferably, at least one compound selected from the formulas (IIc) and (IId) is used as the alkyl glucoside with formula (II).

glucosides having formula (II) are also preferably contained in the preparation according to the invention within certain quantity ranges. It is particularly preferable if the preparation according to the invention contains one or more alkyl glucosides (b) of formula (II) in a total quantity from about 1.2 to about 8.0% by weight %, preferably from about 1.6 to about 6.5% by weight, more preferably from about 2.0 to about 5.0% by weight, and most preferably from about 2.4 to about 3.5% by weight—relative to the total weight of the ready-to-use preparation.

Therefore, a further particularly preferable embodiment of a preparation according to the invention is characterized in that it contains one or more alkyl glucosides (b) of formula (II) in a total quantity from about 1.2 to about 8.0% by weight, preferably from about 1.6 to about 6.5% by weight, more preferably from about 2.0 to about 5.0% by weight, and particularly preferably from about 2.4 to about 3.5% by weight—relative to the total weight of the ready-to-use preparation.

It has also been found that, for the purpose of a covering the smell of ammonia for as long as possible it is advantageous if the alkyl glucosides of formula (I) and the alkyl glucosides of formula (II) are used in certain proportions with respect to one another.

In this context, it is particularly advantageous if the total quantity of the alkyl glucosides of formula (II) used in the ready-to-use preparation is as least twice as great as the total quantity of the alkyl glucosides of formula (I) contained in the ready-to-use preparation In a further most particularly preferable embodiment, a preparation according to the invention is therefore characterized in that the proportion of all alkyl glucosides of formula (I) contained in the ready-to-use preparation to all alkyl glucosides of formula (II) contained in the ready-to-use preparation is in the range from about 1:2 to about 1:10, preferably from about 1:2 to about 1:5.

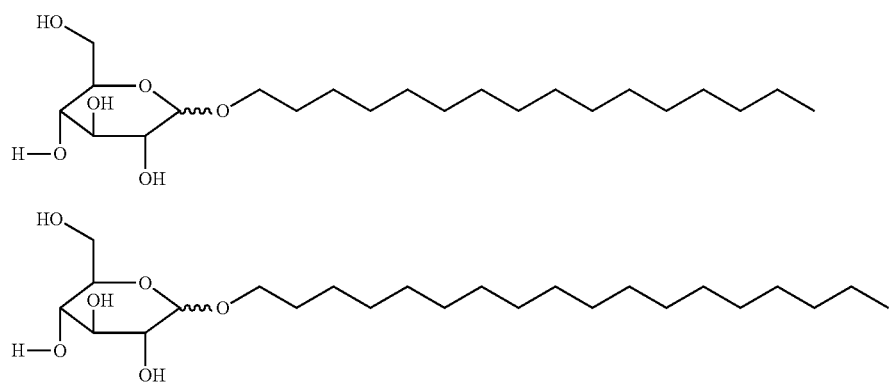

(IIc)

(IId)

In a further particularly preferred embodiment, a preparation according to the invention is characterized in that it contains at least one compound having formula (II) as the second alkyl glucoside (b), in which R2 stands for an unbranched, saturated $C_{16}$ alkyl group or an unbranched, saturated $C_{18}$ alkyl group, and m stands for the number 1.

A particularly preferred alkyl glucoside (b) with R2 equal to a $C_{16}$-$C_{18}$ alkyl group is known by the trade name Montanov 68, for example.

For the purposes of an optimum solution to the problem as defined according to the invention, the one or more alkyl The preparations according to the invention also contain ammonia as an essential alkalising agent for the invention and as a third component (c).

Ammonia is preferably used in the form of the aqueous solution thereof. The corresponding aqueous ammonia solutions may be from about 10 to about 35 percent solutions (calculated in % by weight, 100 g aqueous ammonia solution thus contains 10 to 35 g ammonia). Ammonia is preferably used in the form of about 20 to about 30% by weight solution, particularly preferably in the form of about 25% by weight solution thereof.

It has been found that the perception of the smell of ammonia may be minimised particularly effectively and for a particularly long period of time if ammonia (c) and the other essential components of the formulation (a) and (b) are present in specific proportions with respect to each other. Accordingly, it is particularly preferable if ammonia is used in the preparation according to the invention in a certain quantity range.

In a further, particularly preferable embodiment, and agent for dyeing and/or lightening keratin fibres is therefore characterized in that it contains ammonia (c) in a quantity from about 0.3 to about 5.5% by weight, preferably from about 0.4 to about 4.5% by weight, more preferably from about 0.5 to about 3.5% by weight, and particularly preferably from about 0.6 to about 1.1% by weight—relative to the total weight of the ready-to-use preparation.

The preferable and particularly preferable quantities of ammonia (c) indicated in the preceding assume pure ammonia as the calculation basis. Consequently, if most preferably about 0.6 to about 1.1% by weight ammonia (c) is used in the ready-to-use preparation, this corresponds to the use of a quantity of about 2.4 to about 4.4 g of a 25% by weight ammonia solution in the ready-to-use dyeing and/or lightening agent.

The agents according to the invention are agents for oxidative dyeing and/or agents for oxidative lightening/bleaching hair, and the agents therefore contain at least one oxidiser as a fourth essential component (d) of the formulation.

Usually, hydrogen peroxide is used as the oxidiser. In a preferred embodiment, the hydrogen peroxide is used in the form of an aqueous solution. Ready-to-use preparations that are preferred according to the invention are characterized in that they contain from about 0.5 to about 6.5% by weight, preferably from about 1.3 to about 5.5% by weight, more preferably from about 2.2 to about 5.0% by weight and particularly preferably from about 3.5 to about 4.7% by weight hydrogen peroxide (calculated as 100% $H_2O_2$).

In a further particularly preferable embodiment, an agent for dyeing and/or lightening keratin fibres is therefore characterized in that it contains hydrogen peroxide in a quantity from about 0.5 to about 6.5% by weight, preferably from about 1.3 to about 5.5% by weight, more preferably from about 2.2 to about 5.0% by weight and most particularly preferably from about 3.5 to about 4.7% by weight—relative to the total weight of the ready-to-use preparation—as oxidising agent (d).

Taking into account the preferred and particularly preferred quantity ranges indicated in the preceding of the components (a), (b), (c) and (d) that are essential to the invention, a particularly preferable preparation according to the invention is characterized in that it contains—relative to the total weight of the ready-to-use preparation—
(a) one or more alkyl glucosides of formula (I) in a total quantity from about 0.3 to about 4.5% by weight
(b) one or more alkyl glucosides of Formula (II) in a total quantity from about 1.2 to about 8.0% by weight
(c) about 0.3 to about 5.5% by weight ammonia, and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 1.2 to about 8.0% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 1.2 to about 8.0% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 1.2 to about 8.0% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 1.6 to about 6.5% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 1.6 to about 6.5% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 1.6 to about 6.5% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 1.6 to about 6.5% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 2.0 to about 5.0% by weight
(c) about 0.3 to about 5.5% by weight ammonia and
(d) at least one oxidising agent.

A further particularly preferable preparation is characterized in that it contains—relative to the total weight of the ready-to-use preparation—

(a) one or more alkyl glucosides of formula (I) in a total quantity from about 0.3 to about 4.5% by weight
(b) one or more alkyl glucosides of formula (II) in a total quantity from about 2.0 to about 5.0% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 2.0 to about 5.0% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 2.0 to about 5.0% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 2.4 to about 3.5% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 2.4 to about 3.5% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 2.4 to about 3.5% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.3 to about 4.5% by weight
(b) one or more alkyl glucosides of formula (II) in a total quantity from about 2.4 to about 3.5% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 1.2 to about 8.0% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 1.2 to about 8.0% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 1.2 to about 8.0% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 1.2 to about 8.0% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 1.6 to about 6.5% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 1.6 to about 6.5% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 1.6 to about 6.5% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 1.6 to about 6.5% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to 3.5% by weight
(b) one or more alkyl glucosides of formula (II) in a total quantity from about 2.0 to about 5.0% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 2.0 to about 5.0% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 2.0 to about 5.0% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 2.0 to about 5.0% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 2.4 to about 3.5% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 2.4 to about 3.5% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 2.4 to about 3.5% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.5 to about 3.5% by weight
(b) one or more alkyl glucosides of formula (II) in a total quantity from about 2.4 to about 3.5% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 1.2 to about 8.0% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 1.2 to about 8.0% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 1.2 to about 8.0% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 1.2 to about 8.0% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 1.6 to about 6.5% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 1.6 to about 6.5% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 1.6 to about 6.5% by weight (c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 1.6 to about 6.5% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 2.0 to about 5.0% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 2.0 to about 5.0% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 2.0 to about 5.0% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 2.0 to about 5.0% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 2.4 to about 3.5% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 2.4 to about 3.5% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 2.4 to about 3.5% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.7 to about 2.5% by weight
(b) one or more alkyl glucosides of formula (II) in a total quantity from about 2.4 to about 3.5% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 1.2 to about 8.0% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 1.2 to about 8.0% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 1.2 to about 8.0% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 1.2 to about 8.0% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 1.6 to about 6.5% by weight
(c) about 0.3 to about 5.5% by weight ammonia and
(d) at least one oxidising agent.

A further particularly preferable preparation is characterized in that it contains—relative to the total weight of the ready-to-use preparation—

(a) one or more alkyl glucosides of formula (I) in a total quantity from about 0.9 to about 1.5% by weight
(b) one or more alkyl glucosides of formula (II) in a total quantity from about 1.6 to about 6.5% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 1.6 to about 6.5% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 1.6 to about 6.5% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 2.0 to about 5.0% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 2.0 to about 5.0% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 2.0 to about 5.0% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 2.0 to about 5.0% by weight
(c) about 0.6 to about 1.1% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 2.4 to about 3.5% by weight
(c) about 0.3 to about 5.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 2.4 to about 3.5% by weight
(c) about 0.4 to about 4.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 2.4 to about 3.5% by weight
(c) about 0.5 to about 3.5% by weight ammonia and
(d) at least one oxidising agent.

A further particularly preferable preparation is characterized in that it contains—relative to the total weight of the ready-to-use preparation—
(a) one or more alkyl glucosides of formula (I) in a total quantity from about 0.9 to about 1.5% by weight
(b) one or more alkyl glucosides of formula (II) in a total quantity from about 2.4 to about 3.5% by weight
(c) about 0.6 to about 1.1% by weight ammonia and
(d) at least one oxidising agent.

In the course of the work leading to this invention, it was found that the odour of ammonia may be covered yet more effectively if selected fatty alcohols are also mixed in with the preparation according to the invention in certain quantity ranges.

For the purposes of the invention, fatty alcohols are understood to be saturated or unsaturated, unbranched or branched $C_8$-$C_{28}$ alkyl groups with hydroxyl substitution. Unsaturated fatty alcohols may be monounsaturated or polyunsaturated. The one or more C—C-double bond(s) in an unsaturated fatty alcohol may have the cis or trans configuration thereof.

Fatty alcohols are preferably fatty alcohol with a chain length of at least 20 C atoms. It is particularly preferable to use one or more fatty alcohols from the group consisting of arachyl alcohol (eicosan-1-ol), gadoleyl alcohol ((9Z)-eicos-9-en-1-ol), arachidon alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol).

The fatty alcohols of the group described in the preceding are added to the preparation according to the invention preferably in a total quantity from about 0.5 to about 7.5% by weight, preferably from about 0.7 to about 5.0% by weight, more preferably from about 0.8 to about 4.3% by weight, and particularly preferably from about 0.9 to about 2.6% by weight—relative to the total weight of the ready-to-use preparation.

Consequently, a further particularly preferable embodiment of the invention is characterized in that it also contains one or more fatty alcohols from the group consisting of arachyl alcohol (eicosan-1-ol), gadoleyl alcohol ((9Z)-eicos-9-en-1-ol), arachidon alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol) in a total quantity from about 0.5 to about 7.5% by weight, preferably from about 0.7 to about 5.0% by weight, more preferably from about 0.8 to about 4.3% by weight and particularly preferably from about 0.9 to about 2.6% by weight—relative to the total weight of the ready-to-use preparation.

Besides the fatty alcohols listed previously, the preparations according to the invention may also contain other fatty alcohols with a short alkyl chain length of 12 to 18 C-atoms.

Suitable fatty alcohols from the group of alcohols with a chain length from 12 to 18 C-atoms may be selected from the group consisting of lauryl alcohol (dodecan-1-ol), myristyl alcohol (tetradecan-1-ol), cetyl alcohol (hexadecan-1-ol) and stearyl alcohol (octadecan-1-ol).

The fatty alcohols with a chain length from 12 to 18 C atoms may be used in the preparations according to the in invention in a total quantity from about 0.4 to about 7.5% by weight, preferably from about 0.8 to about 6.6% by weight, more preferably from about 1.2 to about 4.6% by weight and particularly preferably from about 1.6 to about 2.6% by weight—relative to the total weight of the ready-to-use preparation.

In a further embodiment, a preparation according to the invention is therefore characterized in that the it also contains one or more fatty alcohols from the group consisting of lauryl alcohol (dodecan-1-ol), myristyl alcohol (tetradecan-1-ol), cetyl alcohol (hexadecan-1-ol) and stearyl alcohol (octadecan-1-ol) in a total quantity of about 0.4 to about 7.5% by weight, preferably from about 0.8 to about 6.6% by weight, more preferably from about 1.2 to about 4.6% by weight, and particularly preferably from about 1.6 to about 2.6% by weight—relative to the total weight of the ready-to-use preparation.

Surprisingly, however, it was found that the covering of the ammonia smell is reduced and thus also becomes less effective if the fatty alcohols are used in the preparations according to the invention in excessive quantities. For the purpose of solving the problem to be addressed by the invention, it is therefore of advantage if the fatty alcohols contained in the preparations do not exceed a certain total quantity.

Consequently, a further preferable embodiment of the preparation according to the invention is characterized in that the total quantity of all fatty alcohols from the group consisting of arachyl alcohol (eicosan-1-ol), gadoleyl alcohol ((9Z)-eicos-9-en-1-ol), arachidon alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), brassidyl alcohol ((13E)-docosen-1-ol), lauryl alcohol (dodecan-1-ol), myristyl alcohol (tetradecan-1-ol), cetyl alcohol (hexadecan-1-ol) and stearyl alcohol (octadecan-1-ol) contained in the ready-to-use preparation does not exceed 8.0% by weight, preferably 7.0% by weight, more preferably 6.0% by weight and particularly preferably 5.6% by weight—relative to the total weight of the ready-to-use preparation.

Moreover, it is preferable if the preparations according to the invention are oxidative dyeing agents. In this case, the preparations also contain one or more oxidation dye precursors for forming the dyes in the keratin fibres.

In a further preferred embodiment, a preparation according to the invention is characterized in that it additionally contains at least one oxidation dye precursor of the developer type and optionally also at least one oxidation dye precursor of the coupler type.

Oxidation dye precursors include oxidation dye precursors of both the developer type and the coupler type. Particularly suitable oxidation dye precursors of the developer type are selected from at least one compound from the group consisting of p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazol, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically tolerable salts thereof.

Particularly suitable oxidation dye precursors of the coupler type are selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chloorresorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthaline, 2,7-dihydroxynaphthaline, 1,7-dihydroxynaphthaline, 1,8-dihydroxynaphthaline, 4-hydroxyindole, 6-hydroxyindole, 7-hydroxyindole, 4-hydroxyindolin, 6-hydroxyindolin, 7-hydroxyindolin or mixtures of said compounds or the physiologically tolerable salts thereof.

In a preferred embodiment the preparations according to the invention contain one or more oxidation dye precursors in a total quantity from about 0.01 to about 4.0% by weight, preferably from about 0.1 to about 3.5% by weight, more preferably from about 0.6 to about 3.1% by weight, and most particularly preferably from about 1.2 to about 2.2% by weight, relative to the total weight of the ready-to-use preparation.

In a further preferred embodiment, besides the oxidation dye precursors the preparations according to the invention may also contain at least one direct dye for introducing additional colour variations. Direct dyes may be further categorised as anionic, cationic and non-ionic direct dyes. The direct dyes are advantageously selected from nitrophenylene diamines, nitroaminophenols, azo dyes, anthraquinones, triarylmethane dyes or indophenols and the physiologically tolerable salts thereof. The additional direct dyes are each preferably used in a proportion from about 0.001 to about 2% by weight relative to the total application preparation.

Preferred anionic direct dyes are compounds known by the international descriptions or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue. Preferred cationic direct dyes are cationic triphenylmethane dyes such as Basic Blue 7, Basic Blue 26, Basic Violet 2 and Basic Violet 14, aromatic systems that have been substituted with a quaternary nitrogen group, for example Basic Yellow 57, Basic Red 76, Basic Blue 99, Basic Brown 16 and Basic Brown 17, as well as direct dyes containing a heterocycle that comprises at least one quaternary nitrogen atom, particularly Basic Yellow 87, Basic Orange 31 and Basic Red 51. The cationic direct dyes that are marked under the brand name Arianor are also cationic direct dyes that are preferred according to the invention.

Particularly suitable non-ionic direct dyes include non-ionic nitro- and quinone dyes as well neutral azo dyes. Preferred non-ionic direct dyes are compounds known by the international descriptions or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, also 1,4-diamino-2-nitrobenzene, 2-amino-4-nitrophenol, 1,4-bis-(2-hydroxyethyl)amino-2-nitrobenzene, 3-Nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Dyeing results with outstandingly rich colours, shine and good washing fastness are obtained particularly when the preparations according to the invention contain at least one dye selected from D&C Red No. 33 (Acid Red 33), Acid Black No. 1, D&C Orange No. 4 (Acid Orange No. 4), Acid Red 18, Basic Red 76, Acid Violet 43, HC Blue No. 12, N-(2-hydroxethyl)-4-methyl-2-nitroaniline (MethylYellow), HC Yellow No. 2, Red B 54 and 2-amino-6-chloro-4-phenol as an additional direct dye.

As was noted previously, the preparations according to the invention contain ammonia as an alkalising, source and penetrating auxiliary agent. If the ammonia is partly or entirely replaced with alternative, odourless alkalising agents, a variety of drawbacks associated with the application are possible. There, it is advantageous if the preparations according to the invention do not contain certain additional alkalising agents.

The addition of carbonates or bicarbonates is linked to increased hair damage. Therefore, preferred preparations according to the invention are characterized in that they do not contain any carbonates.

For the purposes of the present invention, carbonates are understood to be all salts that contain carbonate or bicarbonate as the anion. This definition also includes inorganic carbonate salts such as sodium carbonate, sodium bicarbonate, potassium carbonate, potassium bicarbonate ammonium carbonate, magnesium carbonate or calcium carbonate.

The carbonate salts of metals or transition metals also fall within the definition of the present invention. The definition of carbonates also encompasses the salts of organic cations (tetraalkylammonium ions, for example) that have a carbonate ($CO_3^{2-}$) or bicarbonate anion ($HCO_3^-$) as the gegenion.

According to the definition, a preparation according to the invention contains no carbonates if the total carbonate content in the preparation according to the invention is less than about 0.1% by weight, preferably less than about 0.05% by weight, particularly preferably less than about 0.01% by weight, and extremely preferably 0% by weight—relative to the total weight of the ready-to-use preparation.

Application problems are still encountered even if ammonia is entirely or partially replaced with alkanolamines. In particular, replacing ammonia with alkanolamines may cause as deterioration in washing fastness and colour variations designed to cover grey.

Alkanolamines are primary, secondary or tertiary amines with a $C_2$-$C_6$ alkyl body that carries at least one hydroxyl functional group. Examples of such alkanolamines include 2-amino ethane-1-ol (monoethanolamine), 2-amino-2-methylpropan-1-ol, 2-amino-2-methyl-1,3-propanediol and triethanolamine.

According to the definition, a preparation according to the invention contains no alkanolamines, if the total alkanolamine content in the in the preparation according to the invention is less than about 0.1% by weight, preferably less than about 0.05% by weight, particularly preferably less than about 0.01% by weight and extremely preferably 0% by weight—relative to the total weight of the ready-to-use preparation.

It is particularly preferable if the preparation according to the invention contains no alkanolamines having the following formula (III).

In a further particularly preferred embodiment, a preparation according to the invention is characterized in that the total quantity of all alkanolamines having formula (III) contained in the ready-to-use preparation—relative to the total weight of the ready-to-use preparation—is less than about 0.1% by weight, preferably less than about 0.05% by weight, more preferably less than about 0.01% by weight and extremely preferably 0% by weight,

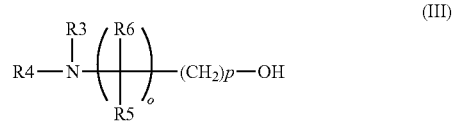

(III)

wherein
radicals R4 and R3 stand independently of one another for a hydrogen atom or a $C_1$-$C_6$ hydroxyalkyl group,
stands for the number 0 or 1,
p stands for a whole number from 1 to 6, and
radicals R5 and R6 stand independently of one another for a $C_1$-$C_6$ alkyl group.

Unlike the alkalising agents described above, the use of small quantities of alkali metal hydroxides has not proven to be detrimental to the properties of the preparation with regard to the ammonia smell and application, so the preparations may contain alkali metal hydroxides (sodium hydroxide and/or potassium hydroxide) in low quantity ranges up to about 1% by weight, preferably up to about 0.5% by weight, and particularly preferably up to about 0.3% by weight—relative to the total weight of the ready-to-use preparation.

The preparations according to the invention may also contain at least one ethoxylated fatty alcohol with a degree of ethoxylation from 25 to 40 as an additional ingredient.

As noted previously, for the present purposes fatty alcohol are understood to be saturated or unsaturated, unbranched or branched $C_8$-$C_{28}$ alkyl groups with hydroxyl substitution. Unsaturated fatty alcohols may a mono- or polyunsaturated. In the case of an unsaturated fatty alcohol the one or more C—C double bond(s) may have the cis- or trans configuration.

Fatty alcohols that are preferred as starting materials for ethoxylation are octan-1-ol (octyl alcohol, capryl alcohol), 1-decanol (decyl alcohol, capric alcohol), 1-dodecanol (dodecyl alcohol, lauryl alcohol), 1-tetradecanol (tetradecyl alcohol, myristyl alcohol), 1-hexadecanol (hexadecyl alcohol, cetyl alcohol, palmityl alcohol), 1-octadecanol (octadecyl alcohol, stearyl alcohol), (9Z)-9-octadecen-1-ol (oleyl alcohol), (9E)-9-octadecen-1-ol (elaidyl alcohol), (9Z,12Z)-octadeca-9,12-diene-1-ol (linoleyl alcohol), (9Z,12Z,15Z)-octadeca-9,12,15-triene-1-ol (linolenoyl alcohol), 1-eicosanol (eicosyl alcohol, arachyl alcohol), (9Z)-eicos-9-en-1-ol (gadoleyl alcohol), (5Z,8Z,11Z,14Z)-eicosa-5,8,11,14-tetraen-1-ol (arachidon alcohol), 1-docosanol (docosyl alcohol, behenyl alcohol), (13E)-1-docosenol (brassidyl alcohol) and (13Z)-docos-13-en-1-ol (erucyl alcohol). Within this group again, 1-hexadecanol (hexadecyl alcohol, cetyl alcohol, palmityl alcohol) and 1-octadecanol (octadecyl alcohol, stearyl alcohol) are most particularly preferred fatty alcohols.

The term ethoxylation (also oxyethylation) is understood to mean the reaction of fatty alcohols with ethylene oxide (EO). Inserting 25 to 40 groups of the type —CH2-CH2-O— for each fatty alcohol molecule causes the formation of linear polyethers that carry a hydroxy group at one end of the chain and the $C_8$-$C_{28}$ alkyl group of the fatty alcohol at the other end of the chain.

The fatty alcohols preferably have a degree of ethoxylation from 26 to 38, more preferably from 27 to 36, and particularly preferably from 28 to 34.

In a further preferred embodiment, a preparation according to the invention is characterized in that it additionally contains at least one ethoxylated fatty alcohol with a degree of ethoxylation from 25 to 40 and which corresponds to formula (IV)

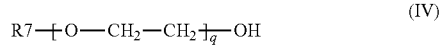

(IV)

and in which

R7 stands for a saturated or unsaturated, unbranched or branched $C_8$-$C_{28}$ alkyl group, preferably for a saturated, unbranched $C_{16}$- or $C_{18}$ alkyl group, and q stands for a whole number from 25 to 40, preferably a whole number from 26 to 38, more preferably for a whole number from 27 to 36 and particularly preferably for a whole number from 28 to 34.

The one or more ethoxylated fatty alcohols with a degree of ethoxylation from 25 to 40 are present in the preparation according to the invention in a total quantity from about 0.2 to about 1.5% by weight, preferably from about 0.3 to about 1.2% by weight, more preferably from about 0.4 to about 0.9% by weight, and particularly preferably from about 0.5 to about 0.8% by weight—relative to the total weight of the ready-to-use preparation.

The ready-to-use dyeing agents may also contain additional active, auxiliary and additive substances in order to improve dyeing performance and to adjust other desired properties of the preparation.

The ready-to-use dyeing agents are advantageously provided in the form of a liquid preparation, so that a surfactant may also be added to the preparations, wherein such surface active substance may be described as tensides or emulsifiers depending on the application area thereof: they are preferably selected from anionic, cationic, zwitterionic, amphoteric and non-ionic tensides and emulsifiers.

Preferred preparations according to the invention are characterized in that the preparation additionally contains at least one anionic tenside. Preferred anionic tensides are fatty acids, alkylsulphates, alkylether sulphates and ether carboxylic acids having 10 to 20 C atoms in the alkyl group, and up to 16 glycol ether groups in the molecule. The anionic tensides are used in proportions from about 0.1 to about 45% by weight, preferably about 1 to about 30% by weight, and most particularly preferably from about 1 to about 15% by weight, relative to the total quantity of the ready-to-use preparation.

Preferred preparations according to the invention are characterized in that the preparation additionally contains at least one zwitterionic tenside. Preferred zwitterionic tensides are betaine, N-alkyl-N,N-dimethylammonium-glycinate, N-acyl-aminopropyl-N,N-dimethylammonium glycinate and 2-alkyl-3-carboxymethyl-3-hydroxyethyl-imidazoline. A preferred zwitterionic tenside is known by the INCI designation cocamidopropyl betaine.

Preferred preparations according to the invention are characterized in that the preparation additionally contains at least one amphoteric tenside. Preferred amphoteric tensides are N-alkylglycine, N-alkylpropionic acids, N-alkylaminobutyric acids, N-alkyliminodipropionic acids, N-hydroxyethyl-N-alkylamidopropyl glycine, N-alkyltaurine, N-alkylsarcosine, 2-alkylaminopropionic acids and alkylaminoacetic acids. Particularly preferred amphoteric tensides are N-cocoalkyl aminopropionate, coco acylamino ethylamino propionate and $C_{12}$-$C_{18}$ acylsarcosine.

It has further proved advantageous if the preparations contain additional, non-ionic surface-active substances, which differ from the non-ionic tensides having formula (IV).

Alkyl polyglycosides and alkylene oxide addition products for fatty alcohols and fatty acids, each with 2 to 30 Mol ethylene oxide per Mol fatty alcohol or fatty acid have proven to be preferred non-ionic tensides. Preparations with excellent properties are also obtained if they contain fatty acid esters of ethoxylated glycerine as the non-ionic tensides.

The non-ionic, zwitterionic or amphoteric tensides are used in proportions from about 0.1 to about 45% by weight, preferably about 1 to about 30% by weight and most particularly preferably from about 1 to about 15% by weight relative to the total quantity of ready-to-use preparations.

Suitable preparations according to the invention may also contain cationic tensides of the quaternary ammonium compound, esterquat and amidoamine types. Preferred quaternary ammonium compounds are ammonium halides and the imidazolium compounds known by the INCI designations Quaternium-27 and Quaternium-83. Quaternised proteinhydrolysates represent other cationic tensides that are usable according to the invention. A particularly suitable compound from the group of amidoamines for the purpose of the invention is the stearamido-propyldimethyl amine available commercially by the name Tegoamid® S 18.

Preferred esterquats are quaternised ester salts of fatty acids with triethanol amine, quaternised ester salts of fatty acids with diethanol alkylamines and quaternised ester salts of fatty acids with 1,2-dihydroxypropyl dialkylamines. The cationic tensides used in the preparations according to the invention are preferably contained in proportions from about 0.05 to about 10% by weight relative to the overall preparation.

The ready-to-use dyes may contain additional auxiliary substances and additives. This, it has proven advantageous if the preparation contains at least one thickening agent. In principle, there are no restrictions regarding such thickening agents. Organic and purely inorganic thickening agents are both equally usable.

Suitable thickening agents are anionic synthetic polymers; cationic synthetic polymers; naturally occurring thickening agents such as non-ionic guar gums, scleroglucan gums or xanthan gums, gum arabic, ghatti gum, karaya gum, gum tragacanth, carrageenan gum, agar-agar, carob gum, pectins, alginates, starch fractions and derivatives such as amylose, amylopectin and dextrins, also cellulose derivatives such as methyl cellulose, carboxyalkyl celluloses and hydroxyalkyl celluloses; non-ionic synthetic polymers such as polyvinyl alcohol or polyvinyl pyrrolidinone; and inorganic thickening agents, particularly phyllosilicates such as bentonite, particularly smectites such as montmorillonite or hectorite.

Dyeing processes typically take place in an alkaline environment. However, in order to avoid exposing the keratin fibres and the skin to harsh conditions as far as possible, it is not advisable to adjust the pH value too high. Thus, it is preferable if the pH value of the ready-to-use preparation is between about 6 and about 11, particularly between about 7 and about 10.5. For the purposes of the present invention, the pH values are pH values that were measured at a temperature of about 22° C.

It has proven to be advantageous if the oxidising preparations according to the invention additionally contain at least one stabiliser or complexing agent to stabilise the hydrogen peroxide. Especially preferred stabilisers are in particular EDTA and EDDS, and phosphonates, particularly 1-hydroxyethane-1,1-diphosphonate (HEDP) and/or ethylene diamine tetramethylene phosphonate (EDTMP) and/or diethylene triamine pentamethylene phosphonate (DTPMP) and sodium salts thereof.

In order to achieve increased lightening and bleaching effect, the preparation may further contain at least one peroxo salt. Suitable peroxo salts are inorganic peroxo compounds, preferably selected from the group consisting of ammonium peroxodisulfate, alkali metal peroxodisulfates, ammonium peroxomonosulfate, alkali metal peroxomonosulfates, alkali metal peroxodiphosphates and alkaline earth metal peroxides.

Particularly preferred are peroxodisulfates, especially ammonium peroxodisulfate, potassium peroxodisulfate and sodium peroxodisulfate.

The persulfates are each contained in the preparation according to the invention in a quantity from about 0.5 to about 20% by weight, preferably about 1 to about 12.5% by weight, particularly preferably about 2.5 to about 10% by weight, and especially about 3 to about 6% by weight, relative to the total weight of the ready-to-use preparation.

The preparations according to the invention may also contain other active and auxiliary substances and additives, such as non-ionic-polymers (for example vinyl pyrrolidinone/vinylacrylate-copolymers, polyvinyl pyrrolidinone, vinylpyrrolidinone/vinylacetate copolymers, polyethylene glycols and polysiloxanes); silicones such as volatile or non-volatile, straight-chain, branched or cyclical, crosslinked or non-crosslinked polyalkyl siloxanes (such as dimethicone or cyclomethicone), polyaryl siloxanes and/or polyalkylaryl siloxanes, particularly polysiloxanes with organofunctional groups, such as substituted or unsubstituted amines (amodimethicone), carboxyl-, alkoxy- and/or hydroxyl groups (dimethicone copolyols), linear polysiloxane(A)-polyoxyalkylene(B)-block copolymers, grafted silicone polymers); cationic polymers such as quaternised cellulose ethers, polysiloxanes with quaternary groups such as dimethyl diallylammonium chloride copolymers, dimethyl aminoethylmethacrylate vinylpyrrolidinone copolymers quaternised with diethyl sulfate, vinyl imidazolinium methochloride copolymers; zwitterionic and amphoteric polymers; anionic polymers such as polyacrylic acids or crosslinked polyacrylic acids; structuring elements such as glucose, maleic acid and lactic acid, hair conditioning compounds such as phospholipids, for example lecithin and cephalin; perfume oils, dimethyl isosorbide and cyclodextrins; active fibre-structure enhancing agents, particularly mono-, di- and oligosaccharides such as glucose, galactose, fructose, fruit sugar and lactose; dyes for colouring the preparation; anti-dandruff ingredients such as piroctone olamine, zinc omadine and climbazol; amino acids and oligopeptides; animal and/or plant-based protein hydrolysates, also derivatives in the form of the fatty acid condensation products or optionally anionically or cationically modified derivatives thereof; vegetable oils, light screening substances and UV blockers; active substances such as panthenol, pantothenic acid, pantolactone, allantoin, pyrrolidinone carboxylic acids and salts thereof, and bisabolol; polyphenols, particularly hydroxycinnamic acids, 6,7-dihydroxycoumarin, hydroxybenzoic acids, catechins, tannins, leucoanthocyanidin, anthocyanidin, flavanones, flavones and flavonols; ceramides or pseudoceramides; vitamins, provitamins and vitamin precursors; plant extracts; greases and waxes such as fatty alcohols, beeswax, montan wax and paraffins; source and penetration substances such as glycerine, propylene glycol monoethyl ether, carbonates, bicarbonates, guanidine, ureas and primary, secondary and tertiary phosphates; opacifiers such as latex, styrene/PVP- and styrene/acrylamide copolymers; pearlescent shine agents such as ethylene glycol mono- and -distearate, also PEG-3-distearate; pigments and propellants such as propane-butane mixtures, $N_2O$, dimethylether, $CO_2$ and air.

A person skilled the art will be equipped to select these further substances according to the desired properties of the preparations. Regarding any other optional components and the quantities to be used of such components reference is herewith made explicitly to the pertinent manuals, which are known to a person skilled in the art. The additional active and auxiliary ingredients are preferably each used in the preparations according to the invention in quantities from about 0.0001 to about 25% by weight, particularly from about 0.0005 to about 15% by weight, relative to the total weight of the application mixture.

The combinations of the previously described alkyl glucosides having formula (I) with alkyl glucosides having formula (II) and optionally selected fatty alcohols are exceptionally well suited for covering the smell of ammonia in preparations for oxidative colouring and oxidative lightening of keratin fibres.

A further object of the present invention is therefore the use of the combination of (a) at least one first alkyl glucoside having formula (I)

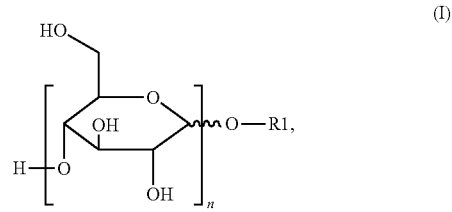

in which R1 stands for an unbranched or branched, saturated or unsaturated $C_{20}$-$C_{28}$ alkyl group, and n stands for a whole number from 1 to 10, and (b) at least one second alkyl glucoside having formula (II)

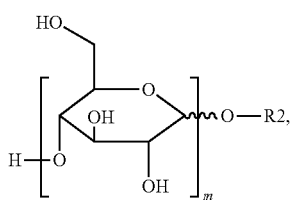

(II)

in which R2 stands for an unbranched or branched, saturated or unsaturated $C_8$-$C_{18}$ alkyl group, and m stands for a whole number from 1 to 10, and (c) optionally at least one fatty alcohol from the group consisting of arachylalcohol (1-eicosanol), gadoleyl alcohol ((9Z)-eicos-9-en-1-ol), arachidon alcohol ((5Z,8Z,11Z, 14Z)-eicosa-5,8,11,14-tetraen-1-ol), heneicosyl alcohol (1-heneicosanol), behenyl alcohol (1-docosanol), erucyl alcohol ((13Z)-docos-13-en-1-ol), brassidyl alcohol ((13E)-docosen-1-ol), lauryl alcohol (1-dodecanol), myristyl alcohol (1-tetradecanol), cetyl alcohol (1-hexadecanol) and stearyl alcohol (1-octadecanol)

for diminishing the smell of ammonia in preparations for oxidative dyeing and/or oxidative lightening of keratin fibres, particularly human hair.

Preparations according to the invention are preferably produced immediately before they are used, from two or more separately packaged substances. This particularly offers the advantage of being able to keep incompatible ingredients separate, thus avoiding a premature reaction. Separation into multicomponent systems is particularly advisable where incompatibilities between the constituent substances are expected or give cause for concern.

In systems of this kind, the ready-to-use preparation is produced by the user by mixing immediately before it is to be used.

In the case of an oxidative dye, it is preferable to provide the preparation in the form of two components packaged separately from one another ("kit of parts"), wherein the first component contains (a) at least one first alkyl glucoside having formula (I)

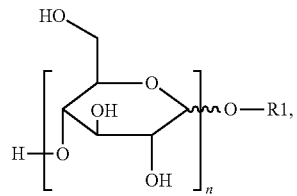

(I)

in which R1 stands for an unbranched or branched, saturated or unsaturated $C_{20}$-$C_{28}$ alkyl group and n stands for a whole number from 1 to 10, (b) at least one second alkyl glucoside having formula (II)

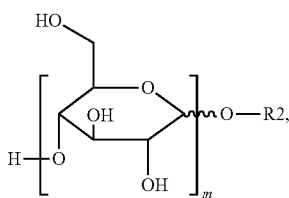

(II)

in which R2 stands for an unbranched or branched, saturated or unsaturated $C_8$-$C_{18}$ alkyl group and m stands for a whole number from 1 to 10, (c) ammonia and additionally at least one oxidation dye precursor of the developer type and optionally also at least one oxidation dye precursor of the coupler type, and wherein the second component (d) contains at least one oxidising agent.

Before use, the first and second components are mixed together very thoroughly, thereby producing the ready-to-use preparation.

All quantity values that refer to the total weight of the ready-to-use preparation are understood to refer to a preparation that (if the preparation according to the invention is provided in the form of components packaged separately from one another) is produced by mixing the various components and is immediately ready for application to the keratin fibre.

Regarding other preferred embodiments of the kit-of-parts according to the invention and uses, the description provided in the preceding text applies mutatis mutandis to the inventive preparations.

1. EXAMPLES

1.1. Production of Ready-to-use Dyes

The following formulations were produced. Unless otherwise indicated, quantities are expressed in percentages by weight.

| Formulation components | V1 (% by weight) | E1 (% by weight) |
|---|---|---|
| Montanov 68 (cetearyl alcohol, cetearyl glucoside) | — | 6.00 |
| Montanov 202 (arachidyl alcohol, behenyl alcohol, arachidyl glucoside) | — | 2.00 |
| Liquid paraffin | 7.40 | 7.40 |
| Lanette 22 (INCI: behenyl alcohol) | 1.80 | 1.80 |
| Lanette D (INCI: cetearyl alcohol) | 1.30 | 1.30 |
| Eumulgin B 3 (INCI: ceteareth-30) | 1.30 | 1.30 |
| Product W 37194 (N,N,N-trimethyl-3-[(1-oxo-2-propenyl)amino]-1-propanaminium chloride, polymer with sodium 2-propenoate) (INCI: acrylamidopropyltrimonium chloride/acrylate copolymer) | 2.00 | 2.00 |
| p-toluenediamine sulfate | 1.50 | 1.50 |
| Resorcinol | 0.58 | 0.58 |
| m-aminophenol | 0.16 | 0.16 |
| 3-amino-2-methylamino-6-methoxypyridine | 0.05 | 0.05 |
| Potassium hydroxide (50%) | 0.7 | 0.7 |
| Vitamin C | 0.05 | 0.05 |
| Hydroxyethane-1,1-diphosphonic acid 60% | 0.20 | 0.20 |
| Sodium silicate 42 (3.1 $SiO_2$: $Na_2O$) | 0.5 | 0.5 |
| Ammonia (25% by weight aqueous solution) | 5.80 | 5.80 |
| Perfume | 0.40 | 0.40 |
| Water | to 100 | to 100 |

V1 is a formulation for comparison purposes, E1 is a formulation according to the invention. The dye creams were each mixed in a ratio of 1:1 with the following oxidising formulation (OX).

| Formulation components | OX (% by weight) |
|---|---|
| Phosphoric acid 85% | 0.04 |
| Hydrogen peroxide (50% ige, aqueous solution) | 12.00 |
| Emulgade F (INCI: cetearyl alcohol, PEG-40 castor oil, sodium cetearyl sulfate) | 2.10 |
| Sodium benzoate | 0.04 |
| Disodium pyrophosphate | 0.30 |
| Ethylenediamine tetraacetate, disodium salt | 0.15 |
| Water | to 100 |

1.2. Determination of Ammonia Smell

The previously prepared application mixtures (V1+OX, E1+OX) were each applied to the head of an experiment participant. During each application period, the ammonia smell was evaluated by 5 trained individuals at different times (immediately after the application after 0 min. after 10 min, after 20 and after 30 min). Evaluations were carried out blind, which means that the individual who made the evaluation did not know which formulation they were evaluating at the time. The value for the preparation was compiled in each case from the individual evaluations.

The ammonia smell was evaluated on a scale from 0 (essentially no perceptible odour) to 10 (very strong smell of ammonia).

TABLE 4

| | Ammonia smell during application | | | |
|---|---|---|---|---|
| | after 0 min. | after 10 min. | after 20 min. | after 30 min. |
| V1 + OX | 5.0 | 3.0 | 3.0 | 1.5 |
| E1 + OX | 2.25 | 2.5 | 1.5 | 1.0 |

It is clear that the smell of ammonia was perceived to have been significantly reduced by the use of the formulation according to the invention not only immediately after the formulations were applied, but also after periods of 10 minutes, 20 minutes and 30 minutes.

The invention claimed is:

1. Preparation for oxidative dyeing and/or lightening of keratin fibres comprising in a cosmetic carrier
  (a) a first alkyl glucoside having formula (I)

in which R1 stands for an unbranched or branched, saturated or unsaturated $C_{20}$-$C_{28}$ alkyl group and n stands for a whole number from 1 to 10, (b) a second alkyl glucoside having formula (II)

in which R2 stands for an unbranched or branched, saturated or unsaturated $C_8$-$C_{18}$ alkyl group and m stands for a whole number from 1 to 10,
  (c) ammonia and
  (d) an oxidiser.

2. The preparation according to claim 1, wherein the first alkyl glucoside having formula (I) is present in a total quantity from about 0.3 to about 4.5% by weight, relative to the total weight of the preparation.

3. The preparation according to claim 1, wherein the second alkyl glucoside having formula (II) is present in a total quantity from about 1.2 to about 8.0% by weight, relative to the total weight of the preparation.

4. The preparation according to claim 1, wherein a proportion of all first alkyl glucosides having formula (I) contained in the preparation with respect to all second -alkyl glucosides having formula (II) contained in the preparation is in the range from about 1:2 to about 1:10.

5. The preparation according to claim 1, wherein the ammonia (c) is present in a quantity from about 0.3 to about 5.5% by weight, relative to the total weight of the preparation.

6. The preparation according to claim 1, wherein the oxidizer comprises hydrogen peroxide, which is present in a quantity from about 0.5 to about 6.5% by weight, relative to the total weight of the preparation.

7. The preparation according to claim 1, further comprising a fatty alcohol chosen from arachyl alcohol (1-eicosanol), gadoleyl alcohol ((9Z)-eicos-9-en-1-ol), arachidon alcohol ((5Z,8Z,11Z,14Z)-eicosa-5,8,11,14-tetraen-1-ol), heneicosyl alcohol (1-heneicosanol), behenyl alcohol (1-docosanol), erucyl alcohol ((13Z)-docos-13-en-1-ol) and brassidyl alcohol ((13E)-docosen-1-ol) in a total quantity from 0.5 to 7.5% by weight, relative to the total weight of the preparation.

8. The preparation according to claim 1, further comprising a fatty alcohol chosen from lauryl alcohol (1-dodecanol), myristyl alcohol (1-tetradecanol), cetyl alcohol (1-hexadecanol) and stearyl alcohol (1-octadecanol) in a total quantity from about 0.4 to about 7.5% by weight, relative to the total weight of the preparation.

9. The preparation according to claim 1, further comprising an oxidation dye precursor of the developer type and optionally in addition thereto an oxidation dye precursor of the coupler type.

10. The preparation according to claim 1, wherein in formula (I)
  R1 stands for an unbranched, saturated $C_{20}$ alkyl group and n stands for the number 1.

11. The preparation according to claim 1, wherein in formula (II)
  R2 stands for an unbranched, saturated $C_{16}$ alkyl group or an unbranched, saturated $C_{18}$ alkyl group, and m stands for the number 1.

12. The preparation according to claim 1, wherein a total content of all fatty alcohols chosen from arachyl alcohol (1-eicosanol), gadoleyl alcohol ((9Z)-eicos-9-en-1-ol), arachidon alcohol ((5Z,8Z,11Z,14Z)-eicosa-5,8,11,14-tetraen-1-ol), heneicosyl alcohol (1-heneicosanol), behenyl alcohol (1-docosanol), erucyl alcohol ((13Z)-docos-13-en-1-ol), brassidyl alcohol ((13E)-1-docosenol), lauryl alcohol (1-dodecanol), myristyl alcohol (1-tetradecanol), cetyl alcohol (1-hexadecanol) and stearyl alcohol (1-octadecanol) is less than about 8.0% by weight, relative to the total weight of the preparation.

13. The preparation according to claim 1, further comprises alkanolamines having formula (III) wherein a total quantity of all alkanolamines contained in the preparation is less than about 0.1% by weight, relative to the total weight of thepreparation,

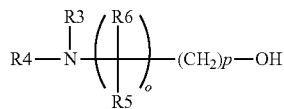

(III)

in which
radicals R4 and R3 independently of one another stand for a hydrogen atom or a $C_1$-$C_6$ hydroxyalkyl group,
o stands for the number 0 or 1,
p stands for a whole number from 1 to 6, and
radicals R5 and R6 independently of one another stand for a $C_1$-$C_6$ alkyl group.

14. The preparation according to claim 1, further comprising an ethoxylated fatty alcohol with a degree of ethoxylation from 25 to 40, and which corresponds to the formula (IV)

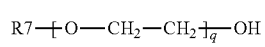

(IV)

and in which
R7 stands for a saturated or unsaturated, unbranched or branched $C_8$-$C_{28}$ alkyl group, and
q stands for a whole number from 25 to 40.

15. A method for oxidative dyeing and/or lightening of keratin fibers comprising appling to the keratin fibers a preparation comprising;

(a) a first alkyl glucoside having formula (I)

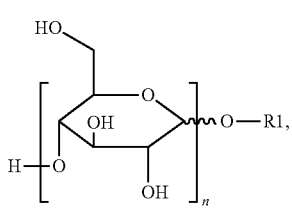

(I)

in which R1 stands for an unbranched or branched, saturated or unsaturated $C_{20}$-$C_{28}$ alkyl group, and
n stands for a whole number from 1 to 10, and
(b) a second alkyl glucoside having formula (II)

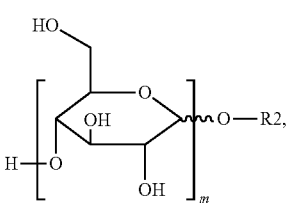

(II)

in which R2 stands for an unbranched or branched, saturated or unsaturated $C_8$-$C_{18}$ alkyl group, and
m stands for a whole number from 1 to 10, and
(c) a fatty alcohol chosen from arachyl alcohol (1-eicosanol), gadoleyl alcohol ((9Z)-eicos-9-en-1 -ol), arachidon alcohol ((5Z,8Z,11Z,14Z)-eicosa-5,8,11,14-tetraen-1-ol), heneicosyl alcohol (1-heneicosanol), behenyl alcohol (1-docosanol), erucyl alcohol ((13Z)-docos-13-en-1-ol), brassidyl alcohol ((13E)-1-docosenol), lauryl alcohol (1-dodecanol), myristyl alcohol (1-tetradecanol), cetyl alcohol (1-hexadecanol) and stearyl alcohol (1-octadecanol)
to reduce a smell of ammonia in preparations for oxidative dyeing and/or oxidative lightening of keratin fibres, particularly human hair.

* * * * *